US006582928B1

(12) United States Patent
Ashkenazi et al.

(10) Patent No.: US 6,582,928 B1
(45) Date of Patent: *Jun. 24, 2003

(54) CARBOHYDRATE-DIRECTED CROSS-LINKING REAGENTS

(75) Inventors: Avi J. Ashkenazi, San Mateo, CA (US); Steven M. Chamow, San Mateo, CA (US); Timothy P. Kogan, Sugar Land, TX (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/517,876

(22) Filed: Mar. 2, 2000

Related U.S. Application Data

(60) Continuation of application No. 09/218,408, filed on Dec. 22, 1998, now Pat. No. 6,124,435, which is a continuation of application No. 08/923,590, filed on Sep. 4, 1997, now Pat. No. 5,929,211, which is a continuation of application No. 08/415,018, filed on Mar. 31, 1995, now Pat. No. 5,889,155, which is a continuation of application No. 08/115,404, filed on Sep. 1, 1993, now abandoned, which is a division of application No. 07/926,077, filed on Aug. 5, 1992, now Pat. No. 5,329,028.

(51) Int. Cl.[7] .................. G01N 33/567; G01N 33/533; G01N 33/564; C07K 1/04; C07D 207/416
(52) U.S. Cl. .................. 435/7.21; 435/960; 435/974; 436/503; 436/546; 436/811; 436/829; 530/408; 530/409; 530/812; 548/545; 548/546; 548/547
(58) Field of Search .................. 548/546, 547, 548/548, 549, 545; 530/351, 391.1, 391.3, 391.5, 391.7, 391.9, 408, 409, 812; 424/450; 436/503, 546, 811, 829; 435/7.21, 960, 974

(56) References Cited

U.S. PATENT DOCUMENTS

| 5,053,520 A | 10/1991 | Biemarz et al. |
| 5,066,490 A | 11/1991 | Neville et al. |
| 5,329,028 A | 7/1994 | Ashkenazi et al. |

FOREIGN PATENT DOCUMENTS

| JP | 42-91155 A | 10/1992 |

OTHER PUBLICATIONS

Heindel et al, Bioconjugate Chem., vol. 2, 427–430, 1991.*
Merriam–Webster Collegiate Dictionary, Tenth Edition, p. 567, Merriam–Webster, Inc. (1996).*
Carlsson, J. et al., "Protein Thiolation and Reversible Protein–Protein Conjugation" *Biochemical Journa* 173:723–737 (1978).
Duncan, R.J.S. et al., "A New Reagent Which May be Used to Introduce Sulfhydryl Groups into Proteins, and Its Use in the Preparation of Conjugates for Immunoassay" *Analytical Biochemistry* 132:68–73 (1983).
Ji, T.H., "Bifunctional Reagents" *Meth. Enzymol.* 91:580–609 (1983).

(List continued on next page.)

*Primary Examiner*—Mary E. Ceperley
(74) *Attorney, Agent, or Firm*—Deirdre L. Conley

(57) ABSTRACT

The invention provides heterobifunctional cross-linking reagents and methods of using the cross-linking reagents. The cross-linking reagents of the invention combine a nucleophilic hydrazide residue with an electrophilic maleimide residue allowing coupling of aldehydes to free thiols. In the methods of the invention, human immunodeficiency virus (HIV) infected cells can be detected using conjugates that include CD4 molecules conjugated to detectable markers via the disclosed cross-linking reagents.

17 Claims, 5 Drawing Sheets

OTHER PUBLICATIONS

Martin, F.J. et al., "Immunospecific Targeting of Liposomes to Cells: A Novel and Efficient Method for Covalent Attachment of Fab[1] Fragments via Disulfide Bonds" *Journal of Biological Chemistry* 257:286–288 (1982).

Rodwell, J.D., "Site–Specific Covalent Modification of Monoclonal Antibodies: In Vitro and In Vivo Evaluations" *Proc. Natl. Acad. Sci. USA* 83:2632–2636 (1986).

Traut, R.R. et al., "Methyl 4–Mercaptobutyrimidate as a Cleavable Cross–Linking Reagent and Its Application to the Escherichia Coli 30S Ribosome" *Biochemistry* 12:3266–3275 (1973).

Webb R.R., II and Kaneko, T., "Synthesis of 1–(Aminooxy)–4–[(3–nitro–2–pyridyl)dithio]butane and 1–(Aminooxy)–4–[(3–nitro–2–pyridyl)dithio]but–2–ene, Novel Heterobifunctional Cross–Linking Reagents" *Bioconjugate Chem.* 1:96–99 (1990).

Zara, J.J. et al., "A Carbohydrate–Directed Heterobifunctional Cross–Linking Reagent for the Synthesis of Immunoconjugates" *Analytical Biochemistry* 194:156–162 (1991).

* cited by examiner

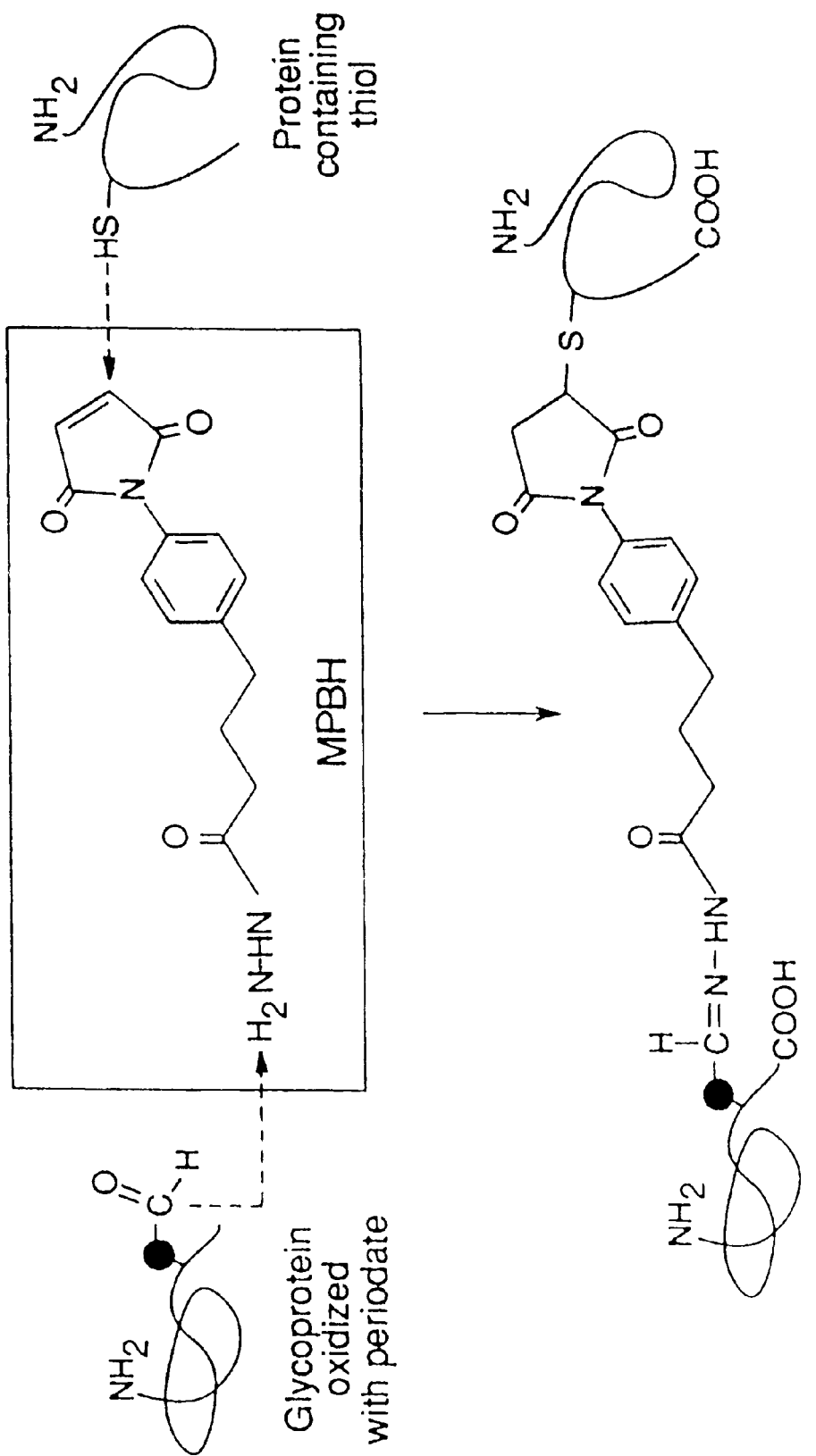
FIG._1

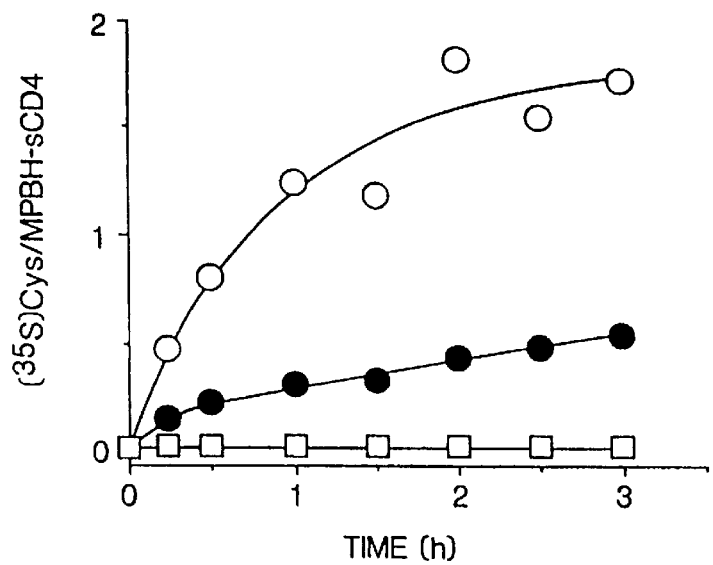
FIG._2
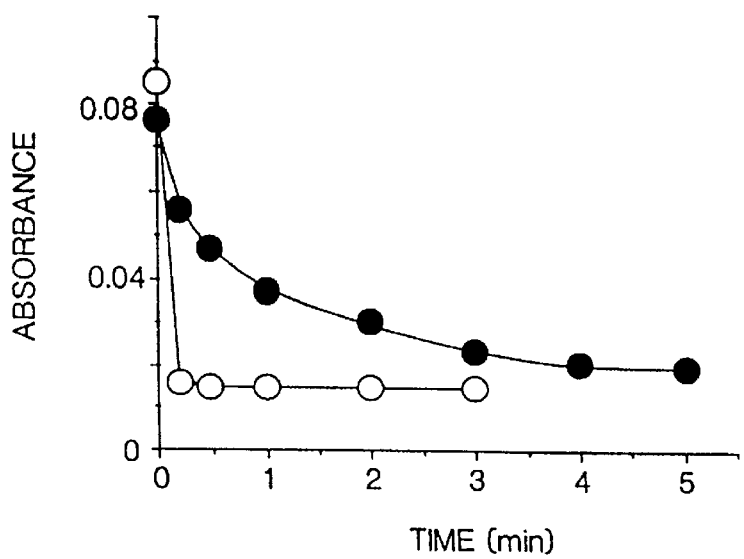
FIG._3A
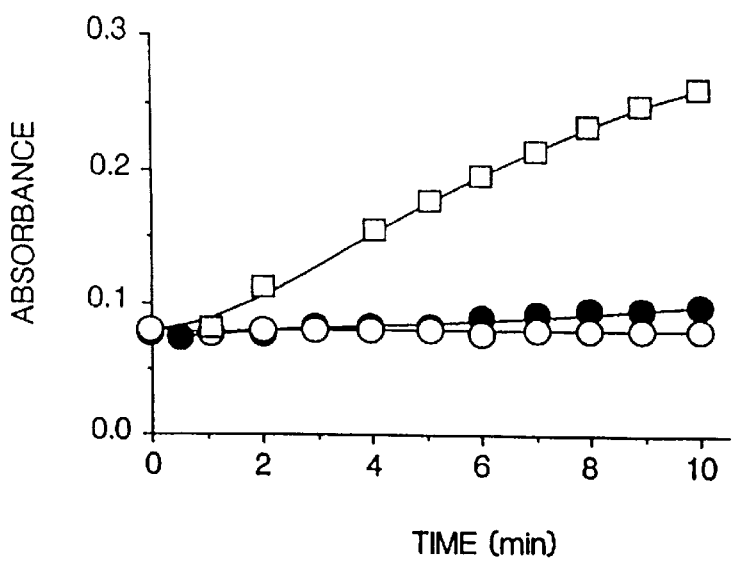
FIG._3B

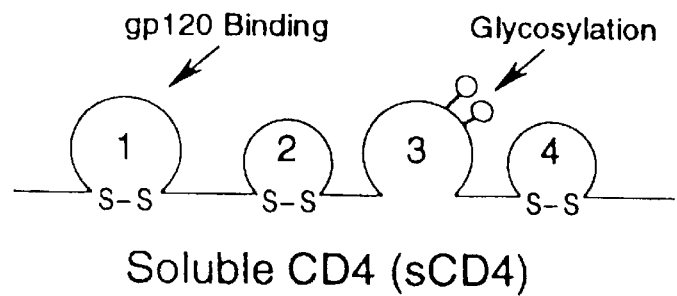
Soluble CD4 (sCD4)
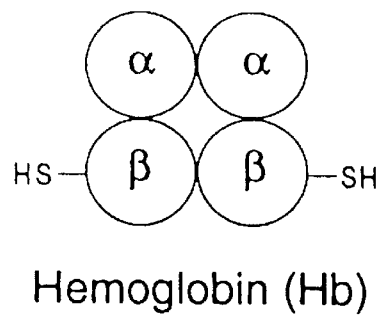
Hemoglobin (Hb)
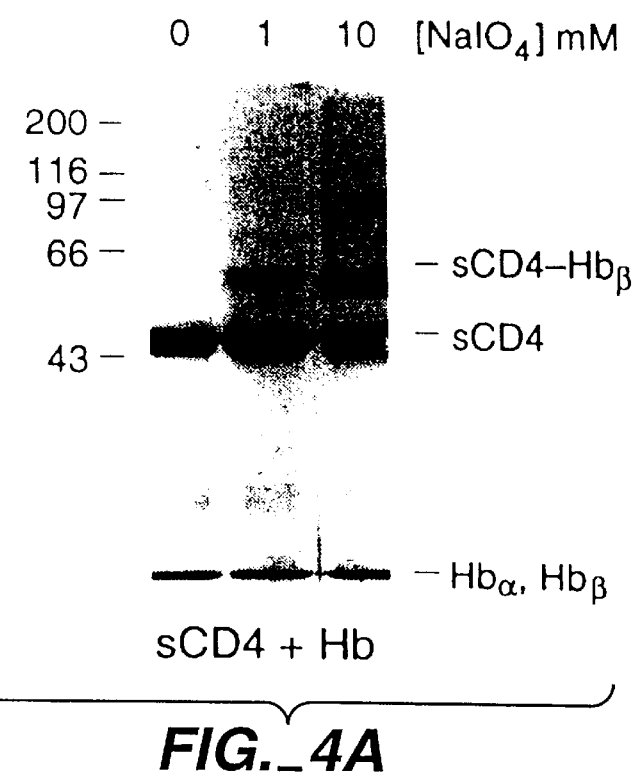
FIG._4A

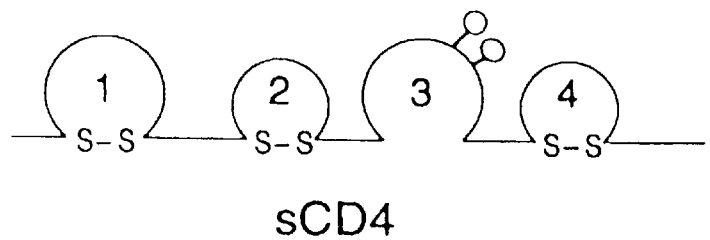
sCD4
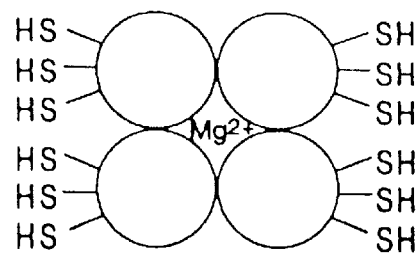
β-Galactosidase (β-gal)
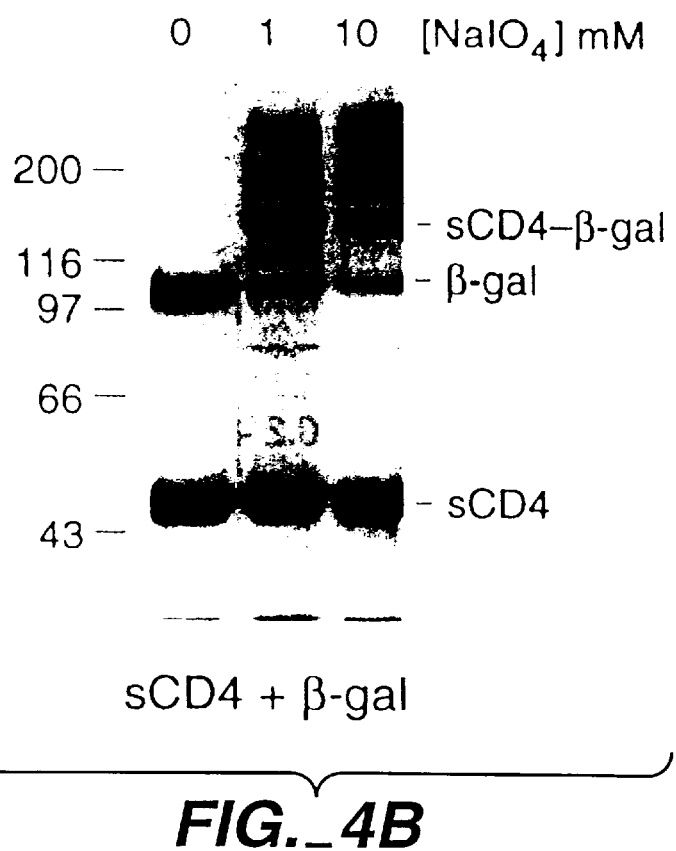
sCD4 + β-gal
FIG._4B

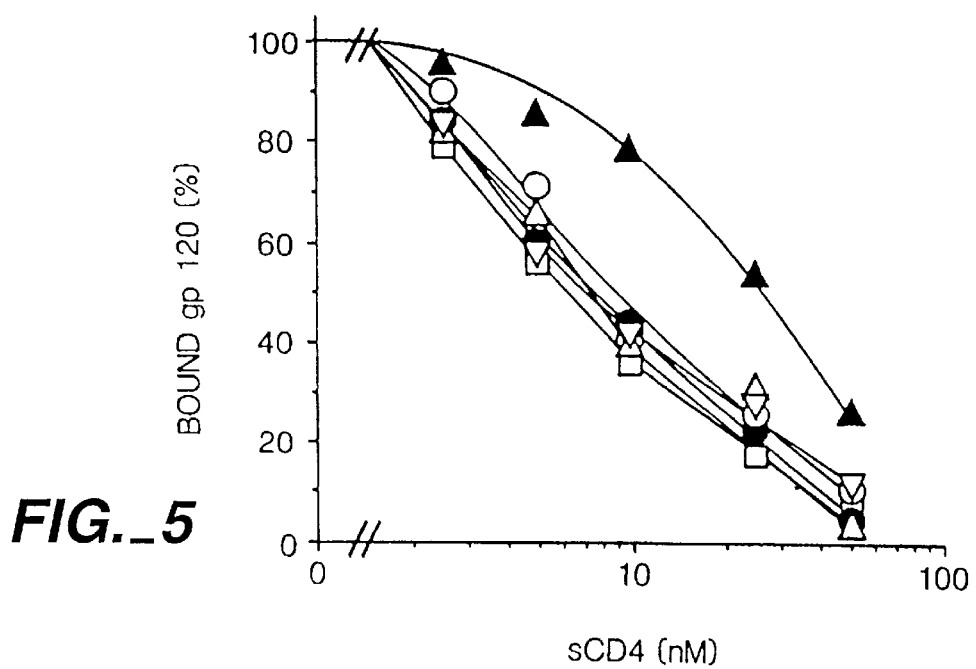
FIG._5
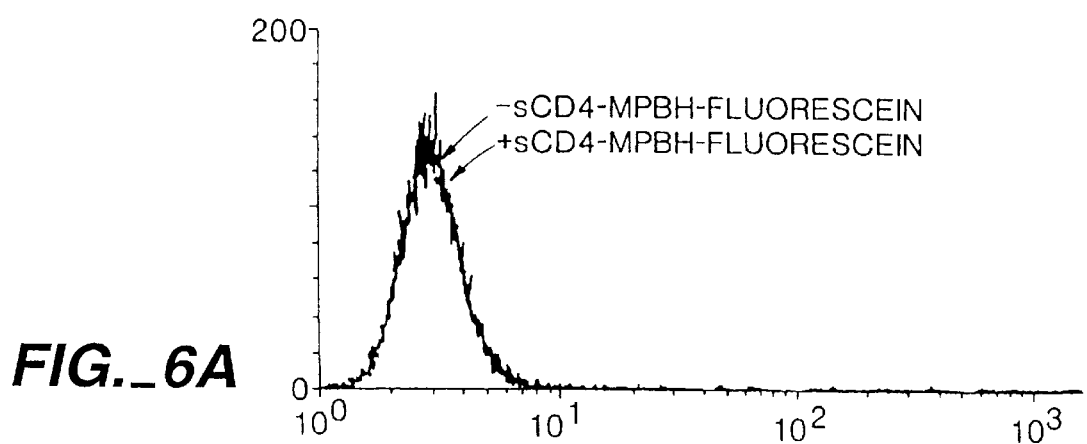
FIG._6A
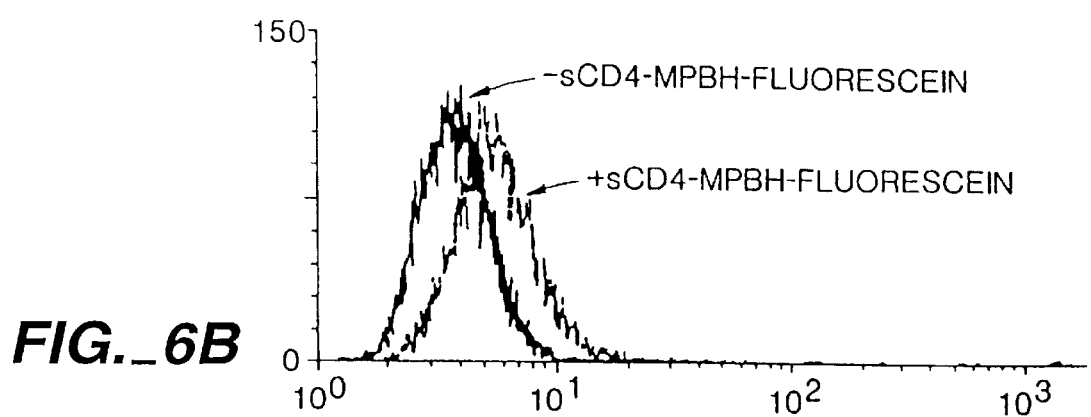
FIG._6B

CARBOHYDRATE-DIRECTED CROSS-LINKING REAGENTS

This application is a continuation application Ser. No. 09/218,408, filed Dec. 22, 1998, U.S. Pat. No. 6,124,435 which is a continuation of application Ser. No. 08/923,590, filed Sep. 4, 1997, issued as U.S. Pat. No. 5,929,211 on Jul. 27, 1999, which is a continuation of application Ser. No. 08/415,018, filed Mar. 31, 1995, issued as U.S. Pat. No. 5,889,155 on Mar. 30, 1999, which is a continuation of application Ser. No. 08/115,404, filed Sep. 1, 1993, now abandoned, which is a divisional application of application Ser. No. 07/926,077, filed Aug. 5, 1992, issued as U.S. Pat. No. 5,329,028 on Jul. 12, 1994, which applications are incorporated herein by reference.

FIELD OF THE INVENTION

The invention is from the field of heterobifunctional cross-linking reagents. More particularly, the invention concerns cross-linking reagents which combine a nucleophilic hydrazide residue with an electrophilic maleimide residue, thereby allowing coupling of aldehydes to free thiols.

BACKGROUND OF THE INVENTION

Bifunctional cross-linking reagents have been extensively used for a variety of purposes including preparation of affinity matrices, modification and stabilization of diverse structures, identification of ligand and receptor binding sites, and structural studies. Homobifunctional reagents which carry two identical functional groups proved to be highly efficient in inducing cross-linking between identical and different macromolecules or subunits of a macromolecule, and linking of polypeptide ligands to their specific binding sites.

Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g. amino, sulfhydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group [For review, see Ji, T. H. "Bifunctional Reagents" in: *Meth. Enzymol.* 91, 580–609 (1983).]

The development of monoclonal antibody technology has created a new demand for bifunctional reagents that are useful in the synthesis of conjugates between antibodies and other proteins or non-proteinaceous molecules, such as detectable markers, toxins, toxin fragments and cytotoxic drugs. However, primary amino groups are randomly distributed on proteins, and therefore, the derivatization with amino-reactive cross-linking agents may impair the protein function, e.g., the antigen binding function of antibodies [Rodwell, J. D., *Proc. Natl. Acad. Sci. USA* 83, 2632–2636 (1986)]. In contrast, covalent modification of antibodies via their carbohydrate portion offers significant advantages. Chemical or enzymatic oxidation of oligosaccharides to aldehydes yields unique functional groups, capable of selective reaction, for example, with amines, hydrazines, hydrazides and semicarbazides, Since the carbohydrate moieties of antibodies are located distal to the antigen binding sites, it has been proposed that they can be modified without significant impairment of the antigen binding function.

Zara, J. J. et al. [*Anal. Biochem.* 194, 156–162 (1991)] describe the synthesis of a heterobifunctional cross-linking reagent, S-(2-thiopyridyl)-L-cysteine hydrazide (TPCH), which contains a hydrazide moiety for coupling to aldehyde groups generated in the carbohydrate residues of antibodies and a pyridyl disulfide moiety for coupling to molecules with a free sulfhydryl (thiol) group. They have demonstrated that derivatization of a human monoclonal IgM antibody against human colon carcinoma cells with 16 TPCH cross-linker molecules did not impair its antigen binding ability.

Heindel, N. D. et al., *Bioconjugate Chem.* 2, 427–430 (1991) describe a maleimide-hydrazide heterobifunctional cross-linking reagent for coupling of thiol groups to formyl groups. Applying this reagent to the coupling of a monoclonal antibody which recognized a nonshed membrane receptor on colon carcinoma, or its Fab' fragment, to polyaldehyde dextran to which an antineoplastic agent had been attached, they found that high binding avidities for the unshed antigen were retained.

Chemical conjugates of recombinant soluble CD4 (sCD4) with toxins, or with antibodies that activate cytotoxic T cells, are also known in the art.

CD4 is a transmembrane glycoprotein, found on the surface of human T lymphocytes, that acts as the primary receptor for HIV-1 [Dalgleish, A. G., et al., *Nature* 312, 763–766 (1984); Klatzmann, D., et al., *Nature* 312, 767–768 (1984)]. The extracellular portion of CD4 contains four immunoglobulin-like domains ($V_1$–$V_4$), the first of which ($V_1$) is necessary and sufficient for high-affinity binding to gp120, the envelope glycoprotein of HIV-1 [Maddon, P. J., et al., *Proc. Natl. Acad. Sci. USA* 84, 9155–9159 (1987); Richardson, N. E., et al., *Proc. Natl. Acad. Sci. USA* 85, 6102–6106 (1988); Landau, N., et al., *Nature* 334, 159–162 (1988)].

Recombinant, soluble forms of CD4 (sCD4), containing only the extracellular portion of the molecule, have been produced [Smith, D. H., et al., *Science* 238, 1704–1707 (1987); Fisher, R. A., Bertonis, et al., *Nature* 331, 76–78 (1988); Hussey, R. E., et al., *Nature* 331, 78–81 (1988); Deen, K. et al., *Nature* 331, 82–84 (1988); Traunecker, A., et al., *Nature* 331, 84–86 (1988); Berger, E., *Proc. Natl. Acad. Sci. USA* 85, 2357–2361 (1988)]. sCD4 retains high-affinity binding to gp120 and can block the binding of HIV-1 to cell surface CD4 in vitro, thereby inhibiting infection of target cells [reviewed in Capon, D. and Ward, R., *Curr. Opin. Immunol.* 2, 433–438 (1990)].

Several modifications of sCD4 have been made, by either gene fusion or chemical conjugation approaches, to expand its antiviral capabilities. One example is a class of chimeric molecules known as CD4 immunoadhesins, in which genes encoding sCD4 and immunoglobulin heavy-chain are combined, thus creating homodimeric antibody-like molecules with properties of both CD4 and human immunoglobulin [Capon, D. et al., *Nature* 337, 525–531 (1989); Zettlmeissl, G., et al., *DNA Cell Biol.* 9, 347–353 (1990); Traunecker, A. et al., *Nature* 339, 68–70 (1989)]. Other notable examples of modified sCD4 are CD4 peptide-protein conjugates [Ghetie, V., *Proc. Natl. Acad. Sci. USA* 88, 5690–5693 (1991)], CD4 electroinserted into erythrocyte membranes [Zeira, M., *Proc. Natl. Acad. Sci. USA* 88, 4409–4413 (1991)], and sCD4-toxin hybrids, in which sCD4 is attached to a toxin either by gene fusion [Chaudhary, V. K., *Nature* 335, 369–372 (1988); Winkler, G., *AIDS Res. Hum. Retroviruses* 7, 393–401 (1991)], or by chemical crosslinking [Till, M. A., *Science* 242, 1166–1168 (1988)].

Because cells infected actively with HIV express gp120 on their surface, sCD4 can be used to direct toxins to, and thus selectively kill, HIV-infected cells. Similarly, bispecific hybrids of sCD4 and anti-CD3 antibody can be constructed which mediate selective killing of HIV-infected cells by cytotoxic T cells [Berg, J., et al., *Proc. Natl. Acad. Sci. USA* 88, 4723–4727 (1991); Idziorek, T., and Klatzmann, D., *AIDS Res. Hum. Retroviruses* 7, 529–536 (1991)].

These examples represent some of the possible modifications of sCD4 which may improve its efficacy against HIV in vivo.

An object of the present invention is to provide improved carbohydrate-directed heterobifunctional cross-linking reagents.

It is another object, to provide chemical conjugates comprising an aldehyde moiety connected to a thiol group via a heterobifunctional cross-linking reagent.

It is a further object, to provide a method for coupling glycoproteins via their carbohydrate moieties to compounds which either contain thiols, or to which thiol groups can be added.

It is yet another object to derivatize members of the immunoglobulin gene superfamily, and in particular antibodies or CD4 molecules in their carbohydrate portion, and to chemically link them to compounds having thiol functional groups or to which thiol groups can be added.

These and further objects of the invention will be apparent for those skilled in the art.

SUMMARY OF THE INVENTION

In one aspect, the invention concerns a heterobifunctional compound of formula (I)

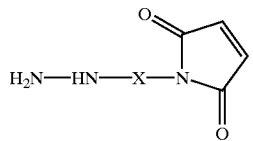

wherein X is a hydrocarbon spacer of 6 to about 25 carbon atoms, or a salt thereof.

The X spacer may be an aliphatic moiety which may optionally comprise an alicyclic, aromatic or heterocyclic moiety, the cyclic components being preferably located near the maleimido functionality of the molecule. The spacer may, alternatively or in addition comprise the residue of any functional groups required for adding the hydrazide or maleimido functionality to the molecule. A preferred compound within the scope of the invention is 4-(4-N-maleimidophenyl)butyric acid hydrazide (MPBH) and its homologues having 2–8 carbon atoms in the aliphatic chain connecting the carbonyl and phenyl groups of the spacer.

In another aspect, the invention concerns a conjugate comprising an aldehyde moiety connected to a thiol group via a heterobifunctional compound as hereinabove described.

In a further aspect, the invention relates to CD4 molecules derivatized by such heterobifunctional compounds.

In a still further aspect, the invention concerns CD4 molecules conjugated, via their carbohydrate portion, to a molecule having a free thiol group or a group convertible to a free thiol group.

In yet another aspect, the invention concerns a method for detecting immunodeficiency virus infected cells, which express the HIV coat glycoprotein, to which CDA binds with high affinity, comprising (a) contacting the cells to be tested with a conjugate comprising a CD4 molecule chemically linked to a detectable marker via a heterobifunctional compound of claim 1, the formula (1) (wherein X is as hereinabove described) and (b) detecting the signal of the marker. Subsequent to their detection, the HIV infected cells, may be isolated or targeted with toxins, cytotoxic agents, etc.

BRIEF DESCRIPTION OF THE DRAWINGS

FIG. 1. Crosslinking with MPBH. MPBH is heterobifunctional, containing hydrazide and maleimide groups, which react with aldehydes and thiols, respectively. Formation of a conjugate between a glycoprotein and a thiol-containing protein is achieved in 3 steps: (a) Oxidation of the carbohydrate chains of the glycoprotein with $NaIO_4$ to generate aldehydes; (b) Condensation of hydrazide and aldehyde, attaching the MPBH reagent to the glycoprotein via a stable hydrazone; and (c) Attachment of a thiol-containing protein to the maleimide-glycoprotein via a thioether linkage to form the complete conjugate. The glycoprotein may be substituted by any glycoconjugate, and the thiol-containing protein by any thiol-containing compound. To facilitate conjugation via this method, thiols can also be added to compounds which lack them [Traut, R. R., et al., *Biochemistry* 12, 3266–3275 (1973); Carlsson, J. et al., *Biochem. J.* 173, 723–737 (1978); Duncan, R. J. S., et al., *Anal. Biochem.* 132, 68–73 (1983).

FIG. 2. Rate and Extent of Addition of MPBH to sCD4, Oxidized Under Mild or Harsh Conditions. sCD4 (1.2 mg/mL), untreated (□), or oxidized under mild (●) or harsh (○) conditions, was incubated at room temperature with 1 mM MPBH in 0.1 M NaOAc pH 5.5. The reaction was stopped by removing excess reagent, and 4 mCi [$^{35}$S]-cysteine in 0.1 M $NaPO_4$ pH 7.0 was added. After 15 min, $^{35}$S-labeled sCD4 was recovered by gel filtration and duplicate aliquots were assayed for radioactivity and protein concentration. sCD4 was assumed to have $M_f$=41,000 [Harris, R. J. et al., *Eur. J. Biochem.* 188, 291–300 (1990).

FIGS. 3B–3B. pH Optimization of MPBH Reaction With Free Thiol. FIG. 3A shows the reaction of MPBH with dithiothreitol. MPBH (230 mM) in 0.1 M buffer was reacted at pH 5.5 (○) or pH 7.0 (●) at room temperature with dithiothreitol (100 mM). The reaction was followed by a decrease in absorbance at 320 nm, resulting from conversion of the maleimide to a thioether. FIG. 3B shows the hydrolysis of MPBH as a function of pH. In this case, absorbance 320 nm increases due to base-catalyzed conversion of the maleimide to maleamic acid, and therefore can be used to monitor the hydrolysis of MPBH. MPBH (230 mM) was incubated in 0.1 M buffer at pH 5.5 (○), pH 7.0 (●), or pH 8.0 (□) at room temperature.

FIGS. 4A–4B Formation of sCD4 Conjugates With Hemoglobin and β-Galactosidase. The four-domain structure of sCD4 and the subunit structures of Hb and β-gal are shown schematically. Domains of sCD4 labeled "1" and "3" are referred to in the text as "$V_1{}^1$" and "$V_3$", respectively. sCD4 was oxidized under the mild (1) or harsh (10) conditions (see "Methods") and reacted with MPBH, then incubated with FIG. 4A Hb or 4B β-gal. Samples in which the oxidation step was omitted (0) represent polypeptides initially present in the reaction mixture. Bands labeled as "sCD4-$Hb_b$" and "sCD4-β-gal" are monovalent conjugates of 66 and 166 kDa, respectively, while bands of higher M, probably represent conjugates that are poly-addition addition products. Reaction products were analyzed by 9% or 7.5% SDS-PAGE, respectively.

FIG. 5. Binding of sCD4 Conjugates to HIV-1 gp120. sCD4 and its derivatives were tested for their ability to compete with immobilized CD4-IgG for the binding of $^{125}$I-labeled gp120. sCD4 (□), sCD4-MPBH produced via the mild (●) or harsh (○) oxidation conditions, sCD4-MPBH-β-gal (Δ), sCD4-MPBH-fluorescein (▽), and sCD4-SMPB (▲). Unconjugated sCD4 was removed from sCD4-MPBH-β-gal by size exclusion chromatography (see the Example).

FIGS. 6A–6B Selective Staining of HIV-1 Infected Cells Using sCD4-MPBH-Fluorescein. sCD4 was conjugated to fluorescein using MPBH, and the resulting sCD4-MPBH-fluorescein was tested for its ability to stain infected CEM.NKR cells in culture, as analyzed by FACS. Uninfected cells FIG. 6A or HIV-1-infected cells FIG. 6B, were incubated in the absence (dashed line) or presence (solid line) of sCD4-MPBH-fluorescein for 30 min on ice. The cells were washed, and green channel fluorescence was determined. For infected cells FIG. 6A, the fluorescence intensity profiles, with or without sCD4-MPBH-fluorescein, were superimposable. For HIV-1-infected cells FIG. 6B, the mean fluorescence intensity was 5.58 and 3.80 for cells incubated with or without sCD4-MPBH-fluorescein, respectively.

DETAILED DESCRIPTION OF THE INVENTION

The present invention was motivated by the desire to develop a new approach for chemical conjugation of sCD4. In our attempts to derivatize sCD4 using conventional cross-linking reagents that attach to amino groups, we found that binding of the derivatized receptor to HIV-1 gp120 was affected adversely. This is probably due to the fact that there is at least one lysine residue in sCD4 which is required for high-affinity binding to gp120 [reviewed in Ryu, S. E., Nature 348, 419–426 (1990); Wang, J. et al., Nature 348, 411–418 (1990)]. Given that (i) residues within the $V_1$ domain of sCD4 are principally responsible for gp120 binding, and that (ii) sCD4 is glycosylated in the $V_3$, but not the $V_1$ domain [Maddon et al., Cell 42, 93–104 (1985)], we reasoned that conjugating sCD4 via its carbohydrate moieties might not affect gp120 binding.

Therefore, we designed a family of novel bifunctional cross-linking reagents which enable the conjugation of sCD4 by reacting with its carbohydrate portion. The new bifunctional cross-linking reagents of the invention are encompassed by the formula (I)

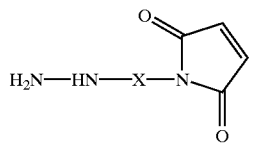

wherein X is a hydrocarbon spacer of 6 to about 25 carbon atoms.

Due to this dual functionality, these cross-linking reagents are suitable for the coupling of glycoproteins, or carbohydrates, other glycoconjugates, to thiol containing proteins or non-proteinaceous compounds. Unlike cross-linking reagents such as N-succinimidyl-4-(p-maleimidophenyl)butyrate (SMPB), which are directed to free amino groups (for review, see Ji, T. H. et al., Meth. Enzymol. 91, 580–608 (1983)), these reagents are carbohydrate-directed. Therefore, in the conjugation of glycoproteins such as sCD4, whose biological activity may be compromised by modification of amino groups, they provide a useful alternative to conventional, amino group-directed cross-linkers.

The most important chemical properties distinguishing the heterobifunctional cross-linkers of the present invention are: (i) their reactive moieties are a hydrazide and a maleimide, a stable nucleophile/electrophile pair; and (ii) these functional groups are separated by a spacer designed to limit the possibility of steric hindrance between the cross-linked compounds [Webb, R. R. II, and Kaneko, T. Bioconjugate Chem. 1, 96–99 (1990)]. The hydrazide and maleimide functional groups were chosen because they provide the desired reactivities with aldehydes and thiols. In addition, these groups are chemically compatible (particularly as the hydrazide hydrochloride), since they do not react with each other spontaneously, and thus self-polymerization of the reagent is prevented. In designing these crosslinkers, we preferred a hydrazide over an amine functionality for reaction with aldehydes (Rodwell, J. D. et al., supra), since the former does not require that the conjugate be reduced. The combination of a hydrazide functional group with maleimide was also found preferred over other thiol-reactive moieties, such as a pyridyl disulfide [Zara, J. J., supra; Martin, F. J., and Papahadjopoulos, D. J. Biol. Chem. 257, 286–288 (1982)], since it forms a stable thioether linkage with, thiols.

We have experimentally demonstrated that a specific compound within the scope herein: 4-(4-N-maleimidophenyl)butyric acid hydrazide (MPBH), generates a stable conjugate by cross-linking carbohydrate-derived aldehydes of a glycoprotein, such as sCD4, to thiol-containing compounds. We have found that sCD4 conjugated with MPBH retains its high binding affinity to gp120 and is capable of labeling HIV-infected cells selectively. Other compounds of formula (I) may be used with similar results.

The results disclosed in the examples demonstrate the ability of the novel cross-linking reagents herein, and specifically MPBH to conjugate a glycoprotein to a thiol-containing protein by producing stable conjugates of sCD4 with hemoglobin (Hb) and β-galactosidase (β-gal). Moreover, we showed that conditions could be tailored to achieve coupling of MPBH selectively through sialic acid residues of sCD4. The sCD4β-gal conjugates were further characterized to determine their gp120 binding affinity relative to unmodified sCD4. The affinity was not changed significantly. Consistent with this finding, the gp120 binding affinity of sCD4 oxidized and coupled to MPBH, or of a sCD4-MPBH-fluorescein conjugate, was also unchanged. Furthermore, sCD4-MPBH-fluorescein was capable of labeling HIV-infected cells selectively, presumably by binding to HIV gp120 expressed on the surface of such cells. These results show that crosslinking of sCD4 to other molecules using MPBH has no adverse effect on its ability to bind to HIV gp120, thus confirming our prediction that conjugation of sCD4 via its carbohydrate moieties would not compromise its biological activity.

In contrast to the sCD4-MPBH conjugates, sCD4 coupled to the amino group-directed cross-linker SMPB exhibited a marked reduction in gp120 binding affinity. Consistent with this result, Till et al., supra, reported a 50–75% reduction in gp120 binding affinity when sCD4 was conjugated to deglycosylated ricin A chain via an amino group-directed cross-linker. This differential effect of cross-linking strategies on affinity illustrates the unique advantage of a carbohydrate-directed cross-linker, such as MPBH, in conjugating to a glycoprotein in which certain amino groups are important for biological function.

Thus, MPBH and its structural analogs facilitate conjugation of sCD4 to anti-HIV agents with no loss of gp120 binding affinity, and therefore, without adverse effects on targeting efficiency and selectivity. In addition to toxins as anti-HIV agents, liposomes containing toxins or agents which can inhibit HIV replication (Matsukura, M. et al., *Proc. Natl. Acad. Sci. USA* 86, 4244–4248 (1989)] may be targeted, via sCD4, to HIV-infected cells. To this end, MPBH has been used to produce sCD4-MPBH-liposomes which bind selectively to HIV-infected-cells [Duzgunes, N. et al., *J. Cell. Biochem. Abst. Supl.* 16E, 77 (1992)].

Indeed, use of MPBH should not be considered only when amino group-directed reagents may compromise the activity of the glycoprotein in question. For example, many cell surface receptors, including those for hormones, growth factors and cytokines, are glycoproteins, and their carbohydrate moieties may be used to cross-link them to neighboring membrane components or to their ligands. Potential conjugation partners, in case they lack free thiols, can be thiolated by simple methods [Traut, R. R. et al., supra; Carlsson, J. et al., supra; Duncan, R. J. S. et al., supra] once they are purified. In addition to glycoproteins, other glycoconjugates, for example, glycophospholipids, should also be amenable to conjugation by this approach.

In the compounds of the present invention the X spacer serves to position the two functional groups at the two ends of the molecule such that they can freely react with the compounds to be cross-linked, and to limit the possibility of steric hinderance is between the cross-linked compounds.

X is defined as a hydrocarbon group of 6 to about 25 carbon atoms. The term "hydrocarbon" is used in the broadest sense and is intended to include spacers in which the hydrocarbon chain is interrupted by one or more heteroatoms, such as sulfur, oxygen or nitrogen. In a specific embodiment, the hydrocarbon is an optionally substituted, saturated or unsaturated, straight or branched chained aliphatic hydrocarbon group of 6 to about 25, more preferably 6 to about 20, even more preferably 6 to about 15, most preferably 6 to about 10 carbon atoms, saturated groups being preferred to avoid the introduction of additional functionalities into the molecule. In another embodiment, the X spacer is composed of a shorter aliphatic hydrocarbon chain and a cyclic moiety, wherein the aliphatic hydrocarbon preferably contains 2 to about 10, more preferably 2 to about 8, most preferably 3 to about 6 carbon atoms, and the cyclic moiety is alicyclic, aromatic or heteroaromatic. The hydrocarbon moiety may be interrupted by at least one heteroatom, and both the hydrocarbon and the cyclic moieties may be substituted. The cyclic groups are preferably located in the proximity of the maleimide functionality (preferably within 3 carbon atoms, more preferably immediately adjacent to the maleimide functionality), and the hydrazide-end of the spacer preferably is the residue of a reactive group capable of reacting with hydrazine or a hydrazine derivative. Such reactive group may, for example, be a carboxyl, in which case its residue is a carbonyl group in the spacer, at the end attached to the hydrazide functionality. The alicyclic moiety present in the spacer may, for example, be a cyclopropyl, cyclobutyl, cyclopentyl, cyclohexyl, cycloheptyl or cyclooctyl group, the cyclohexyl group being preferred. The aromatic moiety preferably is phenyl or substituted phenyl, but may also be a multi-ring aromatic group having a fused or a condensed ring structure, e.g. a naphthyl group. The heterocyclic moiety preferably is a five- or six-membered heterocyclic ring, preferably comprising 1–3, more preferably 2 or 3 heteroatoms selected from oxygen, nitrogen or sulfur. In all instances, unsubstituted groups are preferred, and the substituents, if present, are selected from groups inert under the reaction conditions used in the cross-linking reaction performed with the aid of the bifunctional cross-linking agent herein. Suitable substituents include amino, hydroxyl and nitro groups.

In a particularly preferred group of the compounds of formula (I) the X spacer is an aryl($C_{2-8}$ alkyl)carbonyl, preferably a phenyl($C_{2-6}$ alkyl)carbonyl, most preferably a phenyl($C_{2-4}$ alkyl)carbonyl group, wherein the alkyl moiety is unsubstituted. In this group, the spacer preferably is a 5-phenyl-pentanoyl, 4-phenylbutanoyl, or 3-phenylpropanoyl group.

The compounds of formula (I) are synthesized starting from commercially available or easy to make starting materials by well known reactions of organic chemistry. One possible synthetic route is illustrated in the Example. According to this approach, maleic anhydride is reacted with an amide carrying the desired spacer under conditions required for the condensation reaction that results in the formation of maleimide N-substituted with the spacer. This reaction is preferably performed at reflux temperature, in the presence of a condensing agent, such as pyridine or pyridine derivative. The spacer preferably carries a reactive group capable of reacting with a suitable derivatized hydrazine, or a group convertible to such group. In the specific example provided, the spacer carries a terminal carboxyl group, which is reacted with a reactive ester derivative of hydrazine to yield the desired maleimido hydrazide in which the hydrazide functionality is attached to a carbonyl group. It is easily conceivable that alternative reactions for the introduction of the hydrazide functionality into the molecule are readily available. For example, the functional group at the terminus of the spacer may be an acid halide which can be reacted with a hydrazine or a suitable hydrazine derivative.

It will be appreciated that the spacer can be first attached to either of the functionalities. Part or all of the desired spacer carrying a reactive group, can be first attached to either the maleimide or the hydrazide functional group, and the obtained intermediate can be further reacted with a reactive derivative of the other functionality or with a compound in which the rest of the spacer is attached to the other functionality. There is a great flexibility in the exact way of coupling the maleimide and hydrazide functionalities, and the actual route will largely depend on convenience, and in particular on the availability of the potential starting materials. Based upon the information provided herein, the design of a convenient synthetic route for the preparation of any desired bifunctional cross-linker within the scope of the present invention is well within the knowledge of a person skilled in the art. For example, the compounds of the present invention can be synthesized on the analogy of Scheme I disclosed by Heindel, N. et al., supra, or their preparation can start from the heterobifunctional cross-linking reagents of Zara, J. et al. or from the hydrazide intermediates used in their preparation.

The compounds of formula (I) are preferably synthesized in the form of their acid addition salts, such as hydrochlorides, hydrobromides or hydroiodides, the hydrochlorides being preferred.

The cross-linking reagents of the present invention react with aldehydes and thiols, respectively, and may, for example, be used for linking glycoproteins to thiol-containing compounds or to compounds to which a thiol group can be attached. In this case, the coupling is achieved by: (a) oxidation of the carbohydrate chains of the glycoprotein to aldehyde groups; (b) reaction of the hydrazide functionality of the cross-linker with the aldehyde groups of the glycoprotein to form a stable hydrazone; and (c) attachment of the thiol-containing protein to the maleimide-glycoprotein conjugate via a thioether linkage to form the complete conjugate.

Aldehyde groups can be generated in the carbohydrate residues of glycoproteins or any glycol-containing compounds (e.g. glycoconjugates) by mild chemical or enzymatic oxidation. The chemical oxydation may be performed with a periodate, e.g. sodium metaperiodate, as illustrated in the Example, or as disclosed by Zara, J. et al., supra or Rodwell, J. et al., supra. The glycoprotein preferably is a receptor, more preferably a receptor for a cytokine, a growth factor or a hormone, and most preferably is a member of the immunoglobulin gene superfamily.

In a preferred embodiment, the glycoprotein is a CD4 cell surface receptor, which is linked to an anti-human immunodeficiency virus (HIV) agent having a thiol group or a group convertible to a thiol group. The agent may be comprised in a liposome. In another embodiment, the CD4 molecule is cross-linked with a detectable marker allowing the detection of HIV infected cells.

The glycosylation of glycoproteins is typically either N-linked or O-linked. N-linked refers to the attachment of the carbohydrate moiety to the side-chain of an asparagine residue. The tripeptide sequences, asparagine-X-serine and asparagine-X-threonine, wherein X is any amino acid except proline, are recognition sequences for enzymatic attachment of the carbohydrate moiety to the asparagine side chain. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be involved in O-linked glycosylation. Polypeptides with N- and/or O-linked glycosylation are equally suitable for derivatization by the cross-linkers of the present invention.

The glycosylation pattern of native glycoproteins can be determined by well known techniques of analytical chemistry, including HPAE chromatography [Hardy, M. R. et al., Anal. Biochem. 170, 54–62 (1988)], methylation analysis to determine glycosyl-linkage composition [Lindberg, B., Meth. Enzymol. 28. 178–195 (1972); Waeghe, T. J. et al., Carbohydr. Res. 123, 281–304 (1983)], NMR spectroscopy, mass spectrometry, etc.

Immunoglobulins (Ig) and certain variants thereof are known and many have been prepared in recombinant cell culture. For example, see U.S. Pat. No. 4,745,055; EP 256,654; Faulkner et al., Nature 298:286 (1982); EP 120, 694; EP 125,023; Morrison, J. Immun. 123:793 (1979); K öhler et al., Proc. Nat'l. Acad. Sci. USA 77:2197 (1980); Raso et al., Cancer Res. 41:2073 (1981); Morrison et al., Ann. Rev. Immunol. 2:239 (1984); Morrison, Science 229:1202 (1985); Morrison et al., Proc. Nat'l. Acad. Sci. USA 81:6851 (1984); EP 255,694; EP 266,663; and WO 88/03559. Reassorted immunoglobulin chains also are known. See for example U.S. Pat. No. 4,444,878; WO 88/03565; and EP 68,763 and references cited therein.

Polypeptides encoded by members of the immunoglobulin supergene family (also referred to as immunoglobulin superfamily) contain domains with homology to constant-region domains of immunoglobulins, and include class I and class II major histocompatibility antigens, immunoglobulins and T-cell receptor α, β, γ and chains, such as, for example, CD1, CD2, CD4, CD8, CD28, the γ, and chains of CD3, OX-2, Thy-1, the intracellular or neural cell adhesion molecules (I-CAM or N-CAM), lymphocyte function associated antigen-3 (LFA-3), neurocytoplasmic protein (NPC-3), poly-Ig receptor, myelin-associated glycoprotein (MAG), high affinity IgE receptor, the major glycoprotein of peripheral myelin (Po), platelet derived growth factor receptors (PDGF-A and PDGF-B), colony stimulating factor 1 (CSF-1) receptor, macrophage Fc receptor, Fc gamma receptors and carcinoembryonic antigen [Hood, L. M. et al., Cell 40, 225–229 (1985)]. Homologous as defined herein means having the sequence of a member of the immunoglobulin gene superfamily or having a sequence therewith which has substantially the same as (or a greater degree of) amino acid sequence homology to a known member of the superfamily as the specific examples given above to an immunoglobulin variable or constant domain.

In a preferred embodiment, the conjugates prepared with the aid of the bispecific cross-linkers of the present invention comprise a CD4 amino acid sequence. The amino acid sequence of the native CD4 molecules is known [Maddon et al., Cell 42, 93 (1985)]. The known sequence of the CD4 precursor predicts a hydrophobic signal peptide, an ektra-cellular region of approximately 370 amino acids, a highly hydrophobic stretch with significant identity to the membrane-spanning domain of the class II MHC β chain (transmembrane domain), and a highly charged intracellular sequence of 40 amino acids [Maddon, P., supra]. CD4 is a member of the immunoglobulin superfamily; its extracellular domain contains four contiguous domains, (termed $V_1$, $V_2$, $V_3$, and $V_4$) that resemble the variable regions of immunoglobulins in structure. Truncation of the native CD4 gene to remove the transmembrane and cytoplasmic domain encoding sequences enables the recombinant production of a soluble, secreted protein. It was proposed by several groups that recombinant soluble CD4 (rsCD4) might prevent HIV infection by blocking the virus-receptor interaction. The ability of rsCD4to bind gp120 and thereby block HIV infectivity in vitro has been demonstrated by various authors [Smith et al., Science 238, 1704 (1987); Fisher et al., Nature 331, 37 (1988); Deen et al., Nature 331, 82 (1988); Traunecker et al., 1989, supra].

Several approaches have been used to define the amino acids within the V1 region of the CD4 amino acid sequence to which the gp 120 of the HIV virus binds. These approaches include the technique of random saturation mutagenesis coupled with selection of escape mutants [Peterson and Seed, Cell 54, 65 (1988) and EP 341,444 published Nov. 15, 1989], and homolog-scanning mutagenesis (replacement of sequences from human CD4, which binds gp 120, with unconserved sequences from mouse CD4, which does no bind gp 120) [Landau et al., Nature 334, 159 (1988); Clayton et al., Nature 335, 363 (1988); and WO 89/0322, published Apr. 20, 1989].

As the transmembrane and cytoplasmic regions are not required for the gp 120 binding of CD4, these domains may be deleted to provide a soluble CD4 molecule. Usually at least residues 368 to 395 (the transmembrane domain), and frequently also residues 396 to 433 (the cytoplasmic domain) are deleted.

Insertional variants of CD4 were, for example, published by Mizukami et al., Proc. Natl. Acad. Sci. USA 85, 9273 (1988). Clayton et al., Nature 335, 363 (1988) disclose CD4 variants with individual and multiple substitutions corresponding to regions of the nurine CD4 molecule. Synthetic peptide fragments of CD4 were published by Lifson et al., Science 241, 712 (1988). Peterson and Seed, supra generated several substitution or deletion variants of native CD4 by random mutagenesis. Further CD4 amino acid sequence variants and covalent derivatives are, for example, disclosed in WO 89/02922 published Apr. 6, 1989, and in copending application Ser. No. 07/869,100 filed Apr. 14, 1992 which is a continuation of Ser. No. 07/512,691 filed Apr. 23, 1990. The above-cited U.S. applications specifically disclose CD4 amino acid sequence variants wherein an amino acid has been inserted adjacent to, deleted from, or substituted for an amino acid of CD4 at positions corresponding to position 7, 15, 17,–21,122, 23, 28, 29, 30, 32, 35, 36, 37, 39, 40, 44, 45, 46, 49, 51, 52, 53, 54, 57, 58, 59, 62, 63, 64, 75, 77, 78, 79, 80, 81, 82, 85, 87, 89, 91, or 94 of the native CD4 amino acid sequence. [See also Ashkenazi, A. et al., *Proc. Natl. Acad. Sci. USA* 88, 4723–4727 (1991).]

The carbohydrate structure of CD4, and its recombinant soluble form, including a soluble CD4 produced by recombinant DNA technology, are well known in the art (see, for example, Harris, R. et al., *J. Biochem.* 188, 291–300 (1990); and Spellman, M. et al., *Biochemistry* 30, 2395–2406 (1991)].

The term "CD4" as used herein includes any native CD4 molecule or any derivative or fragment thereof, whether isolated from native source, chemically synthesized or produced by methods of recombinant DNA technology, provided that they retain the qualitative ability to bind the human immunodeficiency virus (HIV). The term "derivative" specifically includes amino acid sequence variants, e.g. substitution, deletion, insertion variants of CD4, and covalent derivatives, such as, for example, derivatives having a glycosylation profile different from a native-sequence. CD4 molecule.

The term "cytokine" is used in a generic sense for proteins released by one cell population which act on another cell as intercellular mediators. Included among the cytokines are growth hormone, insulin-like growth factors, interleukins, hGH, N-methionyl hGH, bovine growth hormone, parathyroid hormone, thyroxine, insulin, proinsulin, relaxin, prorelaxin, glycoprotein hormones such as, follicle stimulating hormone (FSH), thyroid stimulating hormone (TSH), and leutinizing hormone (LH), hemopoietic growth factor, HGF, fibroblast growth factor, prolactin, placental lactogen, tumor necrosis factor-α and -β (TNF-α and -β), mullerian inhibiting substance, mouse gonadotropin-associated peptide, inhibin, activin, vascular endothelial growth factor, integrin, thrombopoietin, nerve growth factors, such as NGF-β, PDGF, transforming growthfactors (TGFs) such as, TGF-α and TGF-β, insulin-like growth factor-1 and -2 (IGF-1 and IGF-2), erythropoietin, osteoinductive factors, interferons (IFNs) such as, IFN-α, IFN-β and IFN-γ, colony stimulating factors (CSFs) such as, M-CSF, GM-CSF, and G-CSF; interleukins (ILs) such as, IL-1, IL-2, IL-3, IL-4, IL-5, IL-6, IL-7, IL-8 and other polypeptide factors. Cytokine receptors are receptors specifically binding to and activated by cytokines as hereinabove defined.

The anti-HIV agent may be any drug known in the art for the prophylaxis or treatment of HIV infection, including AZT, or a moiety capable of recognizing and binding to an activation molecule on the surface of a cytotoxic cell, such as a cytotoxic T cell or large granulocyte lymphocytes (LGL's), thereby redirecting the cytotoxic cells to fight HIV infection. An anti-HIV agent of the latter kind is an anti-CD3 or an anti-CD16 antibody, both of which are known in the art.

Further details of the invention will be provided in the following non-limiting example.

EXAMPLE

Synthesis and Use of 4-(4-N-maleimidophenyl) Butyric Acid Hydrazide (MPBH)

Materials and Methods. Reagents—Human hemoglobin (Hb) was from Sigma (St. Louis, Mo.), *E. coli* β-galactosidase (β-gal) (#567–779, 600–950 U/mg protein) and 2-nitrophenyl-β-D-galactoside were from Boehringer Mannheim (Indianapolis, Ind.), recombinant sCD4 [Smith, D. H. et al., *Science* 238, 1704–1707 (1987); Harris, R. J. et al., supra] and CD4-IgG [Capon, D. J. et al., *Nature* 337, 525–531 (1989)] were purified and characterized at Genentech, SMPB was from Pierce (Rockford, Ill.), and 5-((2 (and -3 -)-S-(acetylmercapto)succinoyl)amino) fluorescein (SAMSA fluorescein, #A-685) was from Molecular Probes (Eugene, Oreg.). Reagents for synthesis of MPBH were from Sigma or Aldrich (Milwaukee, Wis.), and were used without further purification. All other chemicals were of analytical grade.

Synthesis and Characterization of MPBH—Reactions were performed under an inert atmosphere of nitrogen or argon. Spectra were recorded on Nicolet 510 FT-IR (infrared), Varian VXR-300 S (300 MHz) (NMR), and Jeol JMS-HX110HF (mass spectra) spectrometers.

4-Aminophenylbutyric acid (2.0 g, 11.2 mmol) and 2,6-lutidine (1.30 ml, 11.2 mmol) were warmed in tetrahydrofuran (40 ml) to give a homogeneous solution, and were added dropwise over 5 min to a solution of maleic anhydride (1.09 g, 11.2 mmol) in ether (20 ml), heated at reflux. Heating was continued for 30 min and the product was collected by filtration, washed with ether, and vacuum-dried. Acetic anhydride (10 ml) and sodium acetate (0.50 g) were added, and the mixture was heated and stirred at 100° C. (30 min), to obtain a homogeneous brown solution. After cooling, the solution was poured into a mixture of ice and 1 N HCl (50 ml) and extracted with ethyl acetate (2×50 ml). The combined extracts were washed sequentially with water and brine, then dried (MgSO$_4$), and evaporated to give the crude maleimide (2.38 g).

1-(3-Dimethylaminopropyl)-3-ethylcarbodiimide hydrochloride (1.94 g, 10.1 mmol) was added to a solution of the crude maleimide (2.38 g), t-butylcarbazate (1.33 g, 10.1 mmol), and hydroxybenzotriazole (1.36 g, 10.1 mmol), in 30 ml dimethylacetamide, and stirred at room temperature (18 h). The mixture was diluted with 50 ml of water and extracted with ethyl acetate (2×100 ml). The combined extracts were washed sequentially with 1 N HCl, saturated sodium bicarbonate, and brine; then dried (MgSO$_4$), and the solvent removed by evaporation. The product was purified using silica gel HPLC. A 21.4 mm ID×25 cm column was loaded and eluted with a gradient of 1:1 EtOAc/hexane to 7;3 EtOAc/hexane over 40 min at a flow rate of 20 ml/min. The product eluted after 14.7 min (detection at 254 nm), to give 4-(4-N-maleimidophenyl)butyric acid, N-2-t-butyloxycarbonylhydrazide, (1.51 g, 44%), as a pale yellow oil. $^1$H NMR (CDCl$_3$) d 7.40 (br s, 1H, NH), 7.28 (d, J=8.6 Hz, 2H, Ar), 7.25 (d, J=8.6 Hz, 2H, Ar), 6.85 (s, 2H, CH=CH), 6.55 (br s, 1H, NH), 2.71 (t, J=7.6 Hz, 2H, CH$_2$Ph), 2.23 (t, J =7.4 Hz, 2H, CH$_2$CO), 2.02 (m, 2H, CH$_2$), 1.47 (s, 9H, Me$_3$); IR (neat) 3295, 2979, 1714, 1516, 1396, 1244, 1155, 828 (s), 691 (s) cm$^{-1}$; MS (FAB) m/e (rel. abundance) 374 (MH$^+$, 100). Anal. found: C, 60.8; H 6.05; N, 11.2%. C$_{19}$H$_{23}$N$_3$O$_5$ requires C, 61.1; H, 6.2; N, 11.3%.

4-(4-N-Maleimidophenyl) butyric acid, N-2-t-butyloxycarbonylhydrazide (1.50 g, 4.02 mmol) was dissolved in 4 N HCl in dioxane (10 ml) and stirred at room temperature (30 min). Excess HCl was removed by degassing with argon, and the solvent by evaporation. The residue was triturated with ether (3×) and dried under vacuum to give 4-(4-N-maleimidophenyl)butyric acid, hydrazide, hydrochloride (1.02 g, 82%), as a pale yellow powder. $^1$H NMR (d$_6$-DMSO) d 10.4 (br s, 2H, NH$_2$), 7.31 (d, J=8.3 Hz, 2H, Ar), 7.25 (d, J=8.3 Hz, 2H, Ar), 7.18 (s, 2H, CH=CH), 3.45 (br s, 2H, NH$_2$), 2.64 (t, J=7.5 Hz, 2H, CH$_2$Ph), 2.27 (t, J=7.3 Hz, 2H, CH$_2$CO), 1.87 (m, 2H, CH$_2$); IR (KBr) 2940, 1708, 1516 (s), 1401, 1151, 823 (s), 690 (s) cm$^{-1}$; MS (FAB) m/e (rel. abundance) 274 (MH$^+$, 100). Anal. found: C, 54.1; H, 5.1; N, 13.3%. C$_{14}$H$_{15}$N$_3$O$_3$.HCl requires C, 54.3; H, 5.2; N, 13.6%. The final product was determined to be stable for several months if stored dry at 2–8° C., and was freshly dissolved in DMF for use. Oxidation of sCD4 and coupling to MPBH—Two sets of conditions were used for oxidation of the carbohydrate portion of sCD4. sCD4 (10 mg/ml) was oxidized in 0.1 M NaOAc pH 5.5 containing either 1 mM NaIO$_4$ (0.5–3 h, 0° C.) [Van Lenten, L., and Ashwell, G., *J. Biol. Chem.* 246, 1889–1894 (1971)] or 10 mM NaIO$_4$ (0.5–3 h, 23° C.) [O'Shannessy, D. J., and Quarles, R. H. *J. Immunol. Meth.* 99, 153–161 (1987)]. Residual NaIO$_4$ was removed from the oxidized glycoprotein by gel filtration on Sephadex G25 equilibrated in 0.1 M NaOAc pH 5.5. To oxidized sCD4 (1–4 mg/ml) was added MPBH (10 mg/ml in DMF) to a final concentration of 1 mM; conjugation of MPBH to sCD4 proceeded for 0–3 h at 23° C. For gp120 binding studies, the buffer was first exchanged to 0.1 M NaPO$_4$ pH 7.0, 50 mM NaCl; then sCD4-MPBH was reacted with 5 mM 2-mercaptoethanol for 40 min on ice (converting its maleimide moiety to a thioether), then recovered again by gel filtration in the same pH 7.0 buffer. Alternatively, to identify monosaccharides which were oxidized under the two sets of conditions, oxidized sCD4-was recovered free of residual NaIO$_4$ and analyzed for carbohydrate content [Harris, R. J. et al., supra].

Kinetics of MPBH hydrazide coupling to oxidized sCD4—For kinetic measurements, sCD4-MPBH was recovered by gel filtration on Sephadex G25 equilibrated in 10 mM NaOAc pH 5.5, 150 mM NaCl. To sCD4-MPBH (0.5 ml) was added 4 mCi of [$^{35}$S]-cysteine (5.5 GBq/mmol, Amersham) in 0.2 M NaPO$_4$ pH 7.0 (0.5 ml); after 15 min at 23° C, $^{35}$S-labeled glycoprotein was recovered again by gel filtration. To determine specific radioactivity as a means of quantitating the molar ratio of MPBH:sCD4, duplicate aliquots were assayed for radioactivity and for protein concentration [Smith, P. K. et al., supra].

pH optimization of MPBH maleimide reaction—MPBH (230 mM prepared from a 10 mM stock solution in DMF) in 0.1 M sodium acetate pH 5.5, or 0.1 M NaPO$_4$ pH 7.0, was incubated with 100 mM dithiothreitol (5 min, 23° C.) and reaction of the thiol with maleimide to form the thioether was followed by loss of absorbance at 320 nm (e$_{320 nm}$=35.1)$^4$. Hydrolysis of the maleimide of MPBH was measured by incubating MPBH (230 mM) at pH 5.5 or 7.0 (as above), or in 0.1 M sodium borate pH 8.0, and omitting dithiothreitol. Base-catalyzed conversion of the maleimide to maleamic acid [Means, G. E., and Feeney, R. E., *Chemical Modification of Proteins*, pp. 110–114, Holden-Day, San Francisco (1971)] was followed also at 320 nm, but in this case, by an increase in absorbance.

Conjugation of sCD4-MPBH to thiol-containing proteins—Human Hb or *E. coli* b-gal (each 0.4 ml, 5 mg/ml) were coupled to sCD4-MPBH (2 ml, 4 mg/ml), prepared as described above. Coupling was performed pa in 0.1 M NaPO$_4$ pH 7.0 for 2 h at 23° C. β-gal activity was assayed before and after conjugation using 2-nitrophenyl-β-D-galactoside as substrate. Conjugates were analyzed by SDS-PAGE (9% for sCD4-Hb; 7.5% for sCD4-β-gal) [Laemmli, U. K., *Nature* 227, 680–685 (1970)] under reducing conditions and detected by staining with Coomassie blue. For gp120 binding studies, sCD4-β-gal was purified free of residual sCD4 by FPLC size exclusion chromatography on Superose 6 (1×30 cm) equilibrated in 0.1 M sodium phosphate pH 7.0, 50 mM NaCl, 10 mM MgCl$_2$, 1 mM dithiothreitol, and 0.1% Tween-20.

Conjugation of sCD4-MPBH to SAMSA fluorescein—sCD4-MPBH was coupled to SAMSA fluorescein as follows: 2.6 mg of sCD4-MPBH (63 nmol, prepared using the mild oxidation conditions described above), in 1.3 ml of 0.1 M NaPO$_4$ pH 7.0, was mixed with 10 mg of activated SAMSA fluorescein (19 mmol in 1.2 ml of 0.1 M NaPO$_4$ pH 7.0; see below) in a final volume of 2.5 ml. After 30 min at room temperature, sCD4-MPBH-fluorescein (2.6 mg, 0.65 mg/ml) was recovered by gel filtration on Sephadex G25 equilibrated in PBS. SAMSA fluorescein was activated for use as recommended by the manufacturer: 10 mg of SAMSA fluorescein was dissolved in 1 ml of 0.1 N NaOH and incubated at room temperature for 15 min to remove the thiol protecting group. The reagent solution was neutralized (14 ml of 6 N HCl), and buffered by the addition of 0.2 ml of 0.5 M NaPO$_4$ pH 7.0 to give a final reagent solution of 10 mg/1.2 ml, which was used immediately.

Coupling of SMPB to sCD4—sCD4 (3.6 mg/ml) in 0.1 M NaPO$_4$ pH 7.0, 50 mM NaCl was reacted with 1 mM SMPB (10 mg/ml in DMSO) for 1 h at 23° C. As was done for sCD4-MPBH, this step was followed by incubation of sCD4-SMPB for 15 min in 5 mM 2-mercaptoethanol, then recovery by gel filtration in 0.1 M NaPO$_4$ pH 7.0, 50 mM NaCl.

gp120 binding—The ability of sCD4 conjugates to bind to gp120 was determined as described previously (34, 35) [Ashkenazi, A. et al., *Proc. Natl. Acad. Sci. USA* 87, 7150–7154 (1990); Chamow, S. M., et al., *Biochemistry* 29, 9885–9891 (1990)]. Briefly, CD4-IgG [Capon, D. J. et al., supra] was immobilized onto microtiter wells with anti-IgG antibody. Then, sCD4 or its derivative was added simultaneously with $^{125}$I-labeled gp120 (HIV-1$_{IIIB}$) to determine the ability of sCD4 (or derivatized sCD4) to compete with the CD4-IgG for gp120 binding. The assays were done in triplicate; non-specific binding was determined by omitting CD4-IgG.

Labeling CEM cells with sCD4-MPBH-fluorescein—The CEM.NKR T-lymphoblastoid cell line [Howell, D. N. et al., *J. Immunol.* 134, 971–976 (1985)] was infected with HIV-1$_{IIIB}$ as described [Byrn, R. A. et al., *Nature* 344, 667–670 (1990)]. One million viable, HIV-1-infected cells, or uninfected cells, were incubated in 100 ml of sCD4-MPBH-fluorescein (1 mg/ml) in Dulbecco's PBS (GIBCO, Grand Island, N.Y.) containing 2% BSA for 30 min on ice. Control incubations of HIV-1-infected or uninfected cells were performed in PBS-2% BSA (no sCD4-MPBH-fluorescein) under the same conditions. The cells were washed twice with 50 volumes of cold PBS-2% BSA and fixed by incubation in 2% paraformaldehyde in PBS for 24 h at 4° C. Cell fluorescence was measured using a FACStar flow cytometer and LYSIS-II software (Becton-Dickinson,. Mountain View, Calif.).

Results

Design of MPBH—MPBH was designed to cross-link the oligosaccharides of sCD4 to thiol-containing compounds. The reagent (FIG. 1) consists of two reactive moieties, a hydrazide and a maleimide, separated by a 4-phenylbutanoyl spacer. The reaction to form a macromolecular conjugate via MPBH is a 3-step process: (i) oxidation of vicinal diols in the glycoprotein to generate aldehydes in the oligosaccharide portion; (ii) reaction of the aldehydes with the hydrazide function of MPBH to form a hydrazone bond between the glycoprotein and the crosslinking reagent; and (iii) reaction of the maleimide function of MPBH to form a thioether bond with a thiol-containing protein, thus creating a stable glycoprotein-protein conjugate.

Oxidation and Coupling of sCD4 to MPBH—Recombinant human sCD4, expressed in Chinese hamster ovary cells, contains two Asn-linked oligosaccharide chains at Asn-271 and Asn-300 [Maddon, P. J. et al., Cell 42, 93–104 (1985); Harris, R. J. et al., Eur. J. Biochem. 188, 291–300 (1990)]; its carbohydrate composition, on a molar basis, is as follows: fucose, 0.5; N-acetylglucosamine, 6.3; galactose, 4.0; mannose, 7.1; and sialic acid, 2.7 [Harris, R. J. et al., supra]. To identify conditions that might allow incorporation of different amounts of MPBH into sCD4 by selective oxidation of monosaccharides, we compared the effect of mild versus harsh oxidation conditions on the different sugars in sCD4 (Table I). Under the mild conditions (0° C., 1 mM periodate at pH 5.5), only minor degradation of fucose, N-acetylglucosamine, galactose, and mannose residues was observed, whereas sialic acid residues were converted quantitatively to a derivative (probably oxidized at C-7, C-8 and C-9, with loss of C-8 and C-9 as formaldehyde) within 3 h of treatment. Thus, periodate treatment under these conditions appears to oxidize sialic acid residues of sCD4 selectively, consistent with previous work [Van Lenten, L. and Ashwell, G., supra]. In contrast, under the harsh conditions (room temperature, 10 mM periodate, pH 5.5), a more extensive and less selective oxidation of carbohydrates was observed. This is consistent with previous observations upon oxidation of immunoglobulins [O'Shannessy, D. J. and Quarles, R. H., J. Immunol. Meth. 99, 153–161 (1987)]. Sialic acid and fucose were most affected, followed by mannose, galactose, and N-acetylglucosamine, in decreasing order. The concentration of periodate and the temperature of reaction appeared to be the most significant factors in determining the selectivity of oxidation.

We investigated the rate and extent of coupling of MPBH to oxidized sCD4 over a 3 h period by using [$^{35}$S]-cysteine to quantitate the MPBH-maleimides bound to sCD4 (FIG. 2). sCD4 oxidized under mild conditions showed a modest rate of incorporation of MPBH and within 3 h, approximately 0.5 mol of MPBH was incorporated per mol of sCD4. In contrast, sCD4 oxidized under harsh conditions showed significantly more rapid incorporation of MPBH, which began to plateau within 3 h at about 1.7 mol/mol. The lower incorporation of MPBH via the mild oxidation conditions is consistent with fewer aldehydes having formed in the carbohydrate moieties of sCD4 under these conditions (Table I).

To develop the coupling conditions further, we characterized the pH dependency of the rate at which a thiol reacts with the maleimide of MPBH. As might be expected for a reaction in which deprotonated thiol is the nucleophilic species, the rate was rapid at pH 7.0 and slower at pH 5.5 (FIG. 3A). However, MPBH is susceptible to base-catalyzed hydrolysis which converts the maleimide to maleamic acid [Means, G. E. and Feeney, R. E., supra]. To attempt to minimize this, we tested the rate of hydrolysis at several pH values. The hydrolysis was slow at pH 5.5 and 7.0 and markedly more rapid at pH 8.0 (FIG. 3B). Therefore, pH 7.0 appeared to be optimal for thiol addition.

Formation of sCD4-Protein Conjugates—We chose Hb and β-gal as thiol-containing proteins to model the crosslinking ability of MPBH. sCD4 was oxidized under mild or harsh conditions, conjugated via MPBH to Hb or β-gal, and the conjugation products were analyzed by SDS-PAGE (FIG. 4). Hb is a 64 kDa tetramer containing two α and two β subunits associated non-covalently; a single free thiol is present in each of the 16 kDa β-chains. Therefore, sCD4 would be predicted to form a (50+16)=66 kDa covalent species with each Hb β-chain. When the oxidation step was omitted, only the separate polypeptides (sCD4, Hb α- and β-chains) were present (FIG. 4A). However, with mild oxidation of sCD4, reaction with MPBH and Hb resulted in the appearance of a single new band at 66 kDa, indicating the formation of a monovalent sCD4-Hb$_b$ conjugate. When the harsh oxidation conditions were used, several higher M, bands appeared in addition to the 66 kDa band. These bands probably represent the products of poly-addition of Hb$_b$ to sCD4, since under harsh oxidation conditions, multiple MPBH molecules (and thus multiple Hb$_b$ chains) can be incorporated into each molecule of sCD4 (FIG. 2).

β-gal is a homotetramer consisting of 116 kDa subunits associated non-covalently; each subunit contains three free thiols. Thus, conjugation of sCD4 to β-gal could produce a variety of products, ranging from 1 to 3 sCD4 molecules per β-gal subunit. Indeed, SDS-PAGE analysis of sCD4-β-gal conjugation products revealed the presence of multiple bands of $M_r$ equal to or greater than (50+116)=166 (the sum of $M_r$ of sCD4 plus a β-gal subunit) (FIG. 4B). Multiple bands were observed with sCD4 oxidized either under mild or harsh conditions. Notably, mild oxidation of sCD4 resulted in the production of more monovalent sCD4-β-gal conjugate. This is probably due to incorporation of less MPBH into sCD4 under these conditions (FIG. 2), which may limit the extent of the sCD4+β-gal reaction.

Conjugate formation was not quantitative in either the Hb or β-gal case; approximately 30% of the Hb and 80% of the β-gal were crosslinked to the oxidized sCD4. The enzymatic activity of β-gal conjugated to sCD4, as measured by the ability of the enzyme to hydrolyze the synthetic substrate 2-nitrophenyl-β-D-galactoside, was not significantly different from that of unconjugated β-gal (data not shown). This observation is consistent with previous data showing that modification of β-gal via its free thiols does not affect its enzymatic activity [O'Sullivan, M. J. and Marks, V. *Meth. Enzymol.* 73, 147–166 (1981)]. Moreover, it suggests the possibility that conjugation of sCD4 via MPBH to toxins may not affect their enzymatic activity, and thus not compromise their ability to kill target cells.

Effect of sCD4 Conjugation on gp120 Binding—We investigated whether MPBH-mediated coupling via the carbohydrate moieties of sCD4 affects gp120 binding affinity. For comparison, we also tested the binding of sCD4 coupled to SMPB, a reagent which attaches to free amino groups [Martin, F. J. and Papahadjopoulos, D., supra]. sCD4, and sCD4 oxidized under mild conditions and conjugated to MPBH, exhibited similar gp120 binding affinities (FIG. 5). This sCD4-MPBH preparation contained a significant fraction of unconjugated sCD4 (under these oxidation and coupling conditions, the ratio of MPBH incorporation was 0.5 mol/mol; see FIG. 2). Nevertheless, the virtual identity of the competition curves suggests that the sCD4-MPBH conjugate in this preparation bound to gp120 as well as sCD4. Furthermore, sCD4 oxidized under harsh conditions and conjugated to MPBH also bound to gp120 with an affinity similar to sCD4. Based on the data presented in FIG. 2, this preparation of sCD4-MPBH contained little or no unconjugated sCD4 (the ratio of MPBH incorporation was 1.7 mol/mol). Therefore, taken together, these results indicate that conjugation of MPBH to sCD4 does not affect gp120 binding.

We tested also the binding of sCD4-β-gal conjugates to gp120. In preparing conjugates for this purpose, we used the mild oxidation conditions in order to obtain a preparation that was enriched in monovalent sCD4-β-gal conjugate. Also, in this case, we removed unconjugated sCD4 by size exclusion chromatography (see "Methods"). The binding of these purified sCD4-β-gal conjugates to gp120 was similar to that of sCD4 (FIG. 5), demonstrating that actual conjugation of sCD4 to another protein, via MPBH, does not affect its biological activity significantly.

In contrast to the three sCD4-MPBH conjugates described above, which exhibited half maximal inhibition ($IC_{50}$) values ranging from 6–9 nM, sCD4 coupled to SMPB exhibited a markedly lower affinity for gp120 ($IC_{50}$=27 nM) (FIG. 5). Thus, whereas conjugation of sCD4 via its carbohydrate moieties does not appear to affect gp120 binding, conjugation via free amines reduces the gp120 binding affinity significantly.

sCD4-MPBH-Fluorescein Labels HIV-Infected Cells Selectively—To investigate whether a sCD4-MPBH conjugate could be used as a targeting vector that is selective for HIV-1-infected cells, we conjugated sCD4 to a reporter molecule, fluorescein, via MPBH. Binding analysis (FIG. 5) showed that sCD4-MPBH-fluorescein binds gp120 with an affinity comparable to that of unmodified sCD4. Next, we infected human lymphoid CEM cells with HIV-1 (IIIB strain) and tested the ability of sCD4-MPBH-fluorescein to bind to these cells, which remain viable during the assay, by FACS analysis (FIG. 6). Whereas no change in fluorescence was observed upon addition of sCD4-MPBH-fluorescein to CEM cells not exposed to HIV, addition of the conjugate to HIV-infected cells resulted in a significant shift in the mean fluorescence intensity, from 3.8 to 5.6. It should be noted that this preparation of sCD4-MPBH-fluorescein contained some residual, unmodified sCD4. Indeed, a pure preparation of sCD4-MPBH-fluorescein would likely have been even more efficient in selectively labeling HIV-infected cells. Therefore, these results indicate that sCD4, conjugated via its carbohydrate using MPBH, may be used as a selective vector to target cells actively infected with HIV.

All citations cited throughout the specification, and the references cited therein, are hereby expressly incorporated by reference.

Although the foregoing refers to particular preferred embodiments, it will be understood that the present invention is not so limited. It will occur to those of ordinary skill in the art that various modification may be made to the disclosed embodiments without diverting from the overall concept of the invention. All such modifications are intended to be within the scope of the present invention.

TABLE 1

| CARBOHYDRATE | NO OXIDATION* (mol/mol) | MILD OXIDATION (mol/mol) | HARSH OXIDATION (mol/mol) |
|---|---|---|---|
| Fuc | 0.5 | 0.5 | 0.1 |
| GlcNAc | 6.3 | 6.2 | 4.0 |
| Gal | 4.0 | 3.7 | 1.7 |
| Man | 7.1 | 7.1 | 2.8 |
| Sia | 2.7 | 0.1 | 0.0 |

*Data from Harris et al., 1990.

What is claimed is:

1. A conjugate comprising an aldehyde moiety connected to a thiol group via a heterobifunctional compound of formula (I)

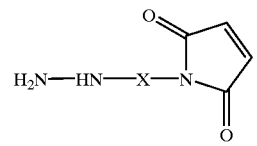

wherein (I) is linked to the aldehyde moiety via the hydrazide group and (I) is linked to the thiol group via the maleimide group, wherein X is a hydrocarbon of 6 to about 25 carbon atoms, or a salt thereof.

2. The conjugate of claim 1 wherein said heterobifunctional compound connects a carbohydrate-containing compound via the aldehyde moiety to a compound having a thiol group or a compound to which a thiol group can be attached.

3. The conjugate of claim 2 wherein said carbohydrate-containing compound is a glycophospholipid.

4. The conjugate of claim 2 wherein said carbohydrate-containing compound is a glycoprotein.

5. The conjugate of claim 2 wherein said compound having a thiol group or a group convertible to a thiol group is a toxin.

6. The conjugate of claim 5 wherein said toxin is in a liposome.

7. The conjugate of claim 4 wherein said glycoprotein is a cell surface receptor.

8. The conjugate of claim 7 wherein said cell surface receptor is a cytokine, a hormone or a growth factor receptor.

9. The conjugate of claim 7 wherein said cell surface receptor is member of the immunoglobulin gene superfamily.

10. The conjugate of claim 9 wherein said cell surface receptor is CD4.

11. The conjugate of claim 10 wherein said compound having a thiol group or to which a thiol group can be attached is an anti-human immunodeficiency virus (anti-HIV) agent.

12. The conjugate of claim 11 wherein said anti-HIV agent is in a liposome.

13. The conjugate of claim 10 wherein said compound having a thiol group or to which a thiol group can be attached is a detectable marker.

14. A method for detecting human immunodeficiency virus (HIV) infected cells, comprising:

(a) contacting the cells to be tested with a conjugate of claim 1, the conjugate comprising a CD4 molecule chemically linked to a detectable marker via the heterobifunctional compound of claim 1; and (b) detecting the signal of said marker.

15. The method of claim 14 comprising additionally isolating said HIV-infected cells.

16. The conjugate of claim 1, wherein X comprises an aliphatic chain and an alicyclic or aromatic moiety.

17. The conjugate of claim 1, wherein X is interrupted by one or more heteroatoms selected from the group consisting of sulfur, oxygen, and nitrogen.

* * * * *